United States Patent [19]

Orsak

[11] Patent Number: 5,683,389
[45] Date of Patent: Nov. 4, 1997

[54] EXTERNAL FIXATOR FOR DISTAL RADIUS FRACTURES

[75] Inventor: James E. Orsak, Memphis, Tenn.

[73] Assignee: Smith & Nephew, Inc., Memphis, Tenn.

[21] Appl. No.: 349,323

[22] Filed: Dec. 5, 1994

[51] Int. Cl.⁶ ............................................. A61B 17/60
[52] U.S. Cl. ................................. 606/59; 606/54
[58] Field of Search ......................... 606/53, 54, 57, 606/59, 55

[56] References Cited

U.S. PATENT DOCUMENTS

| | | | |
|---|---|---|---|
| 3,961,854 | 6/1976 | Jagvet | 606/54 |
| 4,483,334 | 11/1984 | Murray | 606/54 |
| 5,207,676 | 5/1993 | Canadell et al. | 606/54 |
| 5,219,349 | 6/1993 | Krag et al. | 606/54 |
| 5,429,637 | 7/1995 | Hardy | 606/54 |
| 5,443,465 | 8/1995 | Pennig | 606/59 |

FOREIGN PATENT DOCUMENTS 1491492  7/1989  U.S.S.R. ................... 606/53

OTHER PUBLICATIONS

Agee, John M., "External Fixation" Orthopedic Clinics of North America, 24(2), pp. 265–274. Apr. 1993.

*Primary Examiner*—Guy V. Tucker
*Attorney, Agent, or Firm*—Pravel, Hewitt, Kimball & Krieger

[57] ABSTRACT

An external fixator for distal radius fractures provides an elongated support rod that includes proximal and distal rod sections. Radius fixation pins are provided for engaging the patient's radius bone tissue. Radius support clamps are rotatably supported upon the proximal rod section and distal rod section, each of the pins being movable in rotational fashion both with respect to the rod and with respect to the pins.

15 Claims, 6 Drawing Sheets

EXTERNAL FIXATOR FOR DISTAL RADIUS FRACTURES

BACKGROUND OF THE INVENTION

1. Field of the Invention

The present invention relates to orthopedic surgical instrumentation, and more particularly relates to an improved fixator for use in the treatment of distal radius fractures. Even more particularly, the present invention relates to an improved external fixator for the treatment of distal radius fractures that will assist the surgeon in restoring anatomy of a fracture following an injury to the distal radius by allowing the surgeon to quickly manipulate the fixator to apply force to the ligaments in several directions so that the ligaments will reposition the bone fragments in their correct anatomical position and wherein the fixator consists of a bent rod with both ends parallel to each other but offset by a certain distance and multiple pin clamps placed along the rod to secure the rod to the bone.

2. General Background

One of the most common fractures that is treated in emergency rooms is a distal radius fracture sometimes classified as a Colles fracture. One of the popular methods of treating distal radius fractures is to apply an external fixator for the purpose of reducing the fracture by ligamentotaxis, which is a method of distracting the wrist to allow the ligaments to push the bone fragments back in place.

Simple distraction of the wrist is sufficient to restore the original length of the radius, but may not adequately restore other anatomical features such as the tilt angle of the radial head commonly referred to as the radial tilt and the volar tilt.

An example of a technique of multiplanar ligamentotaxis is described by Dr. John Agee in an article published in *Orthopedic Clinics of North America*, Volume 24, No. 2, April 1993 and entitled "External Fixation: Technical Advances Based Upon Multiplanar Ligamentotaxis". John Agee is the named patentee of three (3) United States Patents, namely, U.S. Pat. Nos. 4,548,199; 4,611,586; and 4,922,856. The fixator developed by Dr. Agee provides a method of achieving multiplanar ligamentotaxis through gradual turning of worm screws.

SUMMARY OF THE INVENTION

The present invention provides an improved fixator that allows the orthopedic surgeon to utilize a simple device that will assist in restoring the anatomy of a fracture following an injury to the distal radius by allowing the surgeon to quickly manipulate the fixator to apply force to the ligaments in several directions so that the ligaments will reposition the bone fragments in their correct anatomical position.

The fixator includes a bent rod with both ends parallel to each other but offset by a certain distance. Multiple pin clamps are placed along the rod to secure the rod to the bone. The pin clamps allow rotation around the bar as well as rotation around the clamp to allow the pins to be placed at a wide variety of angles and in multiple planes. A double pin clamp is used to secure pins into the metacarpals of the hand.

The double pin clamp also allows rotation about two axes.

In the preferred embodiment, the pins are secured to the clamp by set screws. However, other clamping methods may be used (for example, clam shell clamps). The restoration of anatomical length is achieved by sliding the metacarpal pin clamp along the rod to distract the ligaments of the wrist.

Restoration of the volar tilt is achieved by loosening the set screws on the metacarpal pin clamp and rotating the rod to allow a vertical translation of the metacarpal pin clamp. Radial tilt can be restored by translating the metacarpal pins through the clamp to shift the wrist sideways. In extreme cases, the rotation can be adjusted by tightening the metacarpal pin clamp to the rod and rotating the rod. The present invention provides an improved fixator apparatus for distal radius fractures that includes an elongated support rod having proximal and distal rod sections joined by a transverse rod section that offsets the proximal and distal rod sections. A pair of bends integrally joins the proximal and distal rod sections to the transverse rod section.

Radius fixation pins are provided for engaging a patient's radius bone tissue.

Radius support clamps are rotatably supported upon the proximal rod section for externally supporting the patient's distal radius, the support clamps including openings that support the radius fixation pins. The support clamps allow rotation relative to the rod and relative to the radius fixation pins.

Metacarpal fixation pins are provided for engaging the patient's metacarpal bone tissue.

Hand support clamps are rotatably supported upon the distal rod section for externally supporting the patient's hand. The hand support clamps include openings for holding the metacarpal fixation pins, the hand support clamps allowing rotation relative to the rod and relative to the metacarpal fixation pins.

The proximal and distal rod sections are generally parallel.

The proximal rod section has a central longitudinal axis and the radius support clamp and rod are so configured that the distal rod section is rotatable during use about the central longitudinal axis of the proximal rod section.

The metacarpal support clamp is slidable along the distal rod section during use for distracting the ligaments of the patient's wrist.

The rod and support clamps are so configured that volar tilt is achieved by rotating the distal rod section relative to the proximal rod section when the support clamps are rotated with respect to the rod.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figures 1, 4:
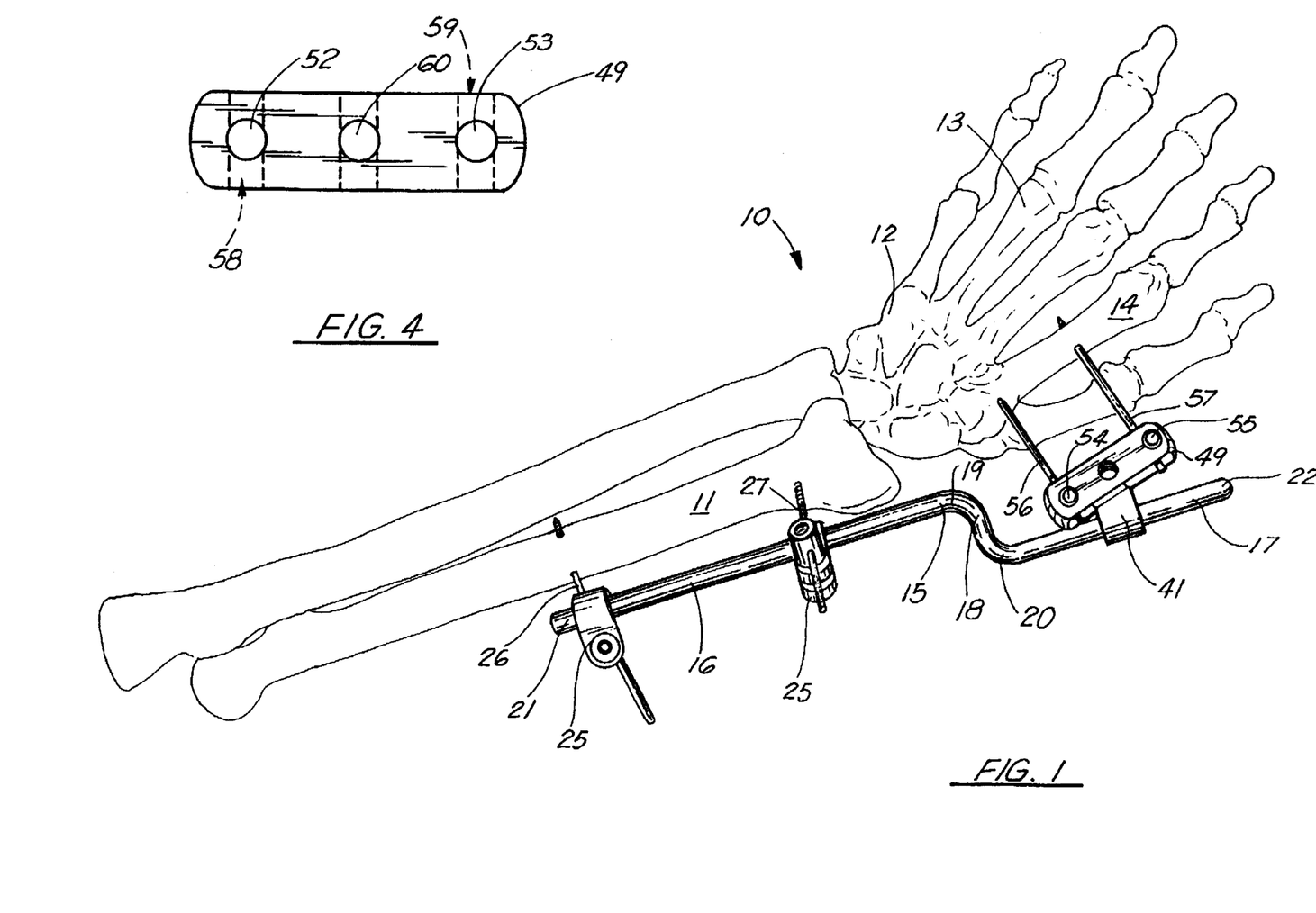
FIG. 1 is a perspective view of a first embodiment of the apparatus of the present invention.
FIG. 4 is a fragmentary top view of the first embodiment of the apparatus of the present invention taken along lines 4—4 for FIG. 3.
Figure 2:
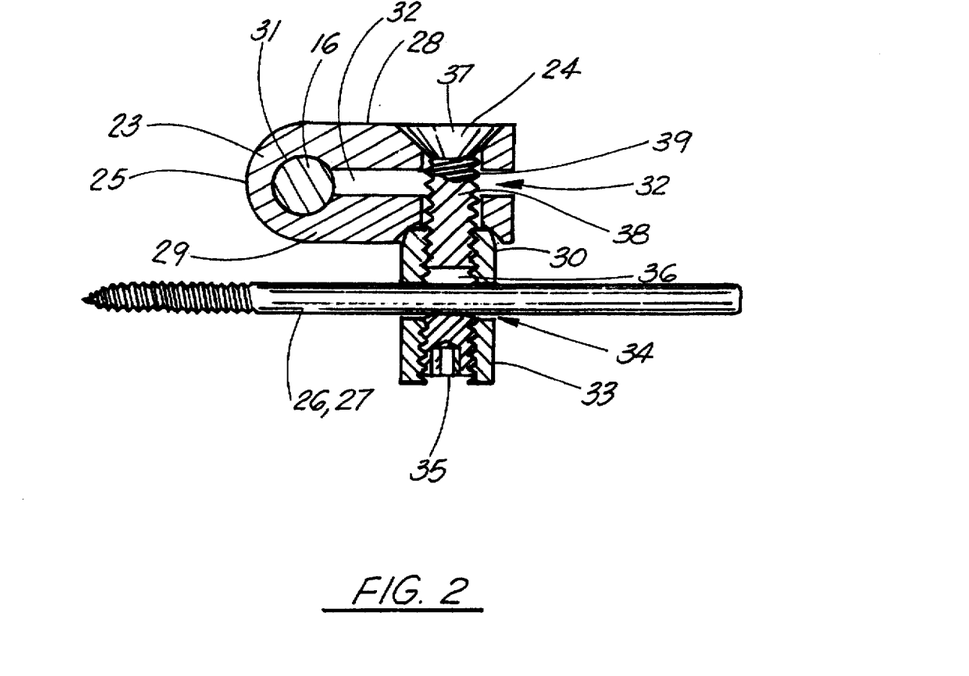
FIG. 2 is a fragmentary view of a first embodiment of the apparatus of the present invention illustrating the radial pin clamp portion thereof.
Figure 3:
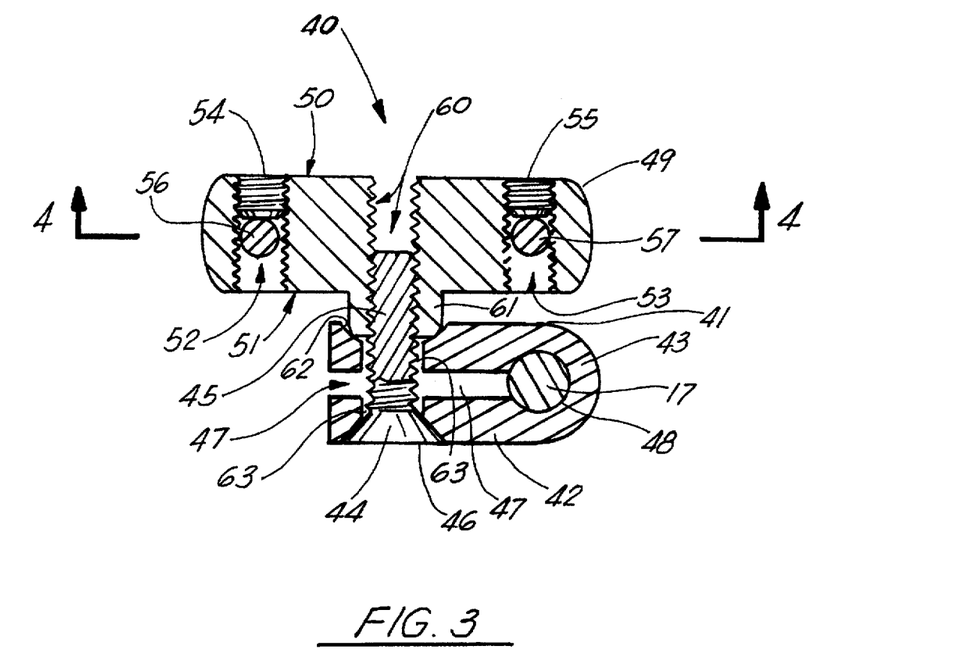
FIG. 3 is a fragmentary view of a first embodiment of the apparatus of the present invention illustrating the metacarpal pin clamp portion thereof.

FIGS. 1–3 show generally the first embodiment of the apparatus of the present invention designated generally by the numeral 10. Distal radius fixator 10 is shown in FIG. 1 attached to a patient's distal radius 11, wrist 12 and hand 13 at metacarpals 14.

An elongated rod 15 includes a proximal rod section 16 and a distal rod section 17. Rod sections 16 and 17 are preferably joined by a transverse rod section 18 and a pair of bends 19, 20 as shown in the drawings. The rod 15 is preferably integrally formed as shown, including proximal and distal rod sections 16, 17, transverse rod section 18, and bends 19, 20. The rod ends 21, 22 can be provided with protective plastic end caps to contain the pin clamps on the rod when the clamps are loose.

Clamps 25 are attached to proximal rod section 16. In FIG. 1, two (2) radius pin clamps 25 are shown in the illustration. Each of the radius pin clamps 25 affixes to the radius bone pins 26, 27 as shown. Each radius pin 26, 27 is surgically connected to the fractured radius 11 as shown. The second embodiment of FIG. 8 also includes rod 15 with its sections 16–18, clamps 25 and pins 26, 27 as will be discussed hereinafter with reference to the description of FIG. 8.

Each pin clamp 25 (FIG. 2) includes a pair of opposed clamp members including upper clamp member 28 and lower clamp member 29. Clamp sections 28, 29 are rotatably affixed to pivot 30. Clamp sections 28, 29 join together at U-shaped portion 23. Slot 32 and cylindrical opening 31 is positioned between sections 28, 29. Opening 31 and slot 32 provide a configuration that secures proximal rod section 16 to clamp 25. Pivot 30 is defined by cap screw 24 and sleeve 33. Sleeve 33 has an opening 34 that accommodates one of the radius pins 26, 27. Sleeve 33 has interval threads that are engaged by threads of set screw 35 and by threads of cap screw 24. Set screw 35 can be tightened to secure a selected radius pin 26, 27 to radius pin clamp 25. Set screw 35 occupies internally threaded bore 36 of sleeve 33.

Cap screw 24 occupies internally threaded bore 36 to define pivot 30. Cap screw 24 has an enlarged frustroconical head 37, threaded shank 38, and external threads 39 that cooperate with the internal threads of sleeve 33 bore.

Metacarpal pin clamp 40 is shown in FIG. 3. Metacarpal pin clamp 40 includes an upper clamp section 41 and a lower clamp section 42. The clamp sections 41, 42 attach to one another at U-shaped portion 43. Cap screw 44 extends through opening 63 in clamp sections 41, 42. Cap screw 44 includes a threaded shank 45 and a frustroconical head 46. A gap 47 and opening 48 are positioned between upper clamp section 41 and lower clamp section 42. Distal rod section 17 occupies opening 48. Shank 45 threadably engages pin holder 49 at threaded opening 60. Pin holder 49 has an upper surface 50 and a lower surface 51.

A pair of threaded openings 52, 53 extending between upper and lower surfaces 50, 51. Set screws 54, 55 respectively engage pins 56, 57. Each of the pins 56, 57 extend through a transverse opening that is generally parallel to upper and lower surfaces 50, 51 (see FIG. 1). Openings 58, 59 intersect threaded openings 52, 53 respectively at generally right angles.

Upon assembly, cap screw 44 engages threaded opening 60. Annular collar 61 engages beveled annular surface 62 of upper clamp section 41. Continued rotation of cap screw 44 pulls upper and lower sections 41, 42 together, clamping rod 17 and attaching pin holder 49 to upper section 41. Opening 63 in clamp sections 41, 42 accommodates cap screw 44 during use.

Figure 7:
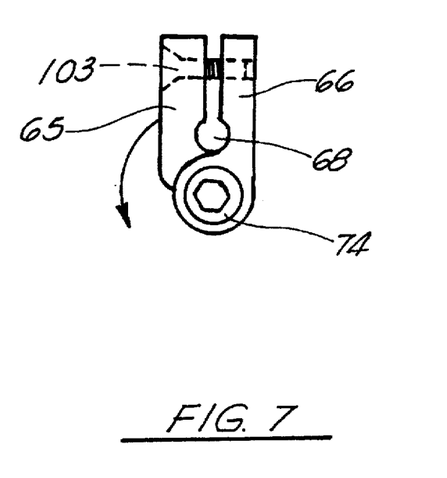
FIG. 7 is a partial sectional view of the second embodiment of the apparatus of the present invention
Figure 8:
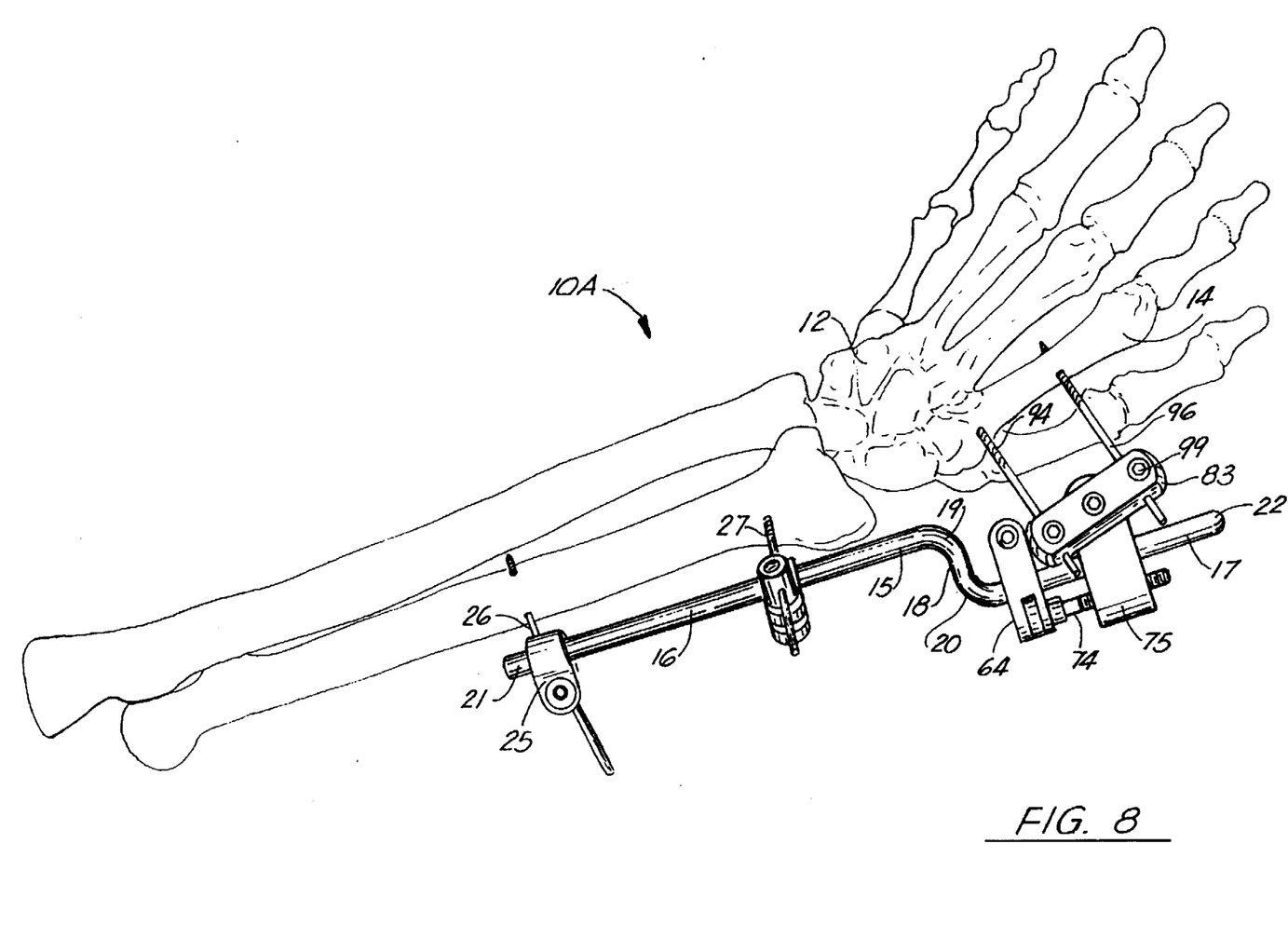
FIG. 8 is a perspective view of the second embodiment of the apparatus of the present invention.

FIGS. 5–10 illustrate the second embodiment of the apparatus of the present invention designated generally in FIG. 8 by the numeral 10A. Distal radius fixator 10A is shown in FIG. 8 as attached to the distal radius 11. Also shown are the patient's wrist bones 12, hand 13 and metacarpals 14.

As with the first embodiment 10, the second embodiment of distal radius fixator 10A uses an elongated rod 15 having a proximal rod section 16, a distal rod section 17, a transverse rod section 18, and a pair of bends 19, 20 that connect the proximal 16 and distal rod sections 17 respectively to the transverse rod section 18. The rod 15 includes ends 21, 22. In the embodiment of FIG. 8, there is also provided a pair of radius pin clamps 25 attached respectively to pins 26, 27 as with the embodiment of FIG. 1.

Figures 9, 10:
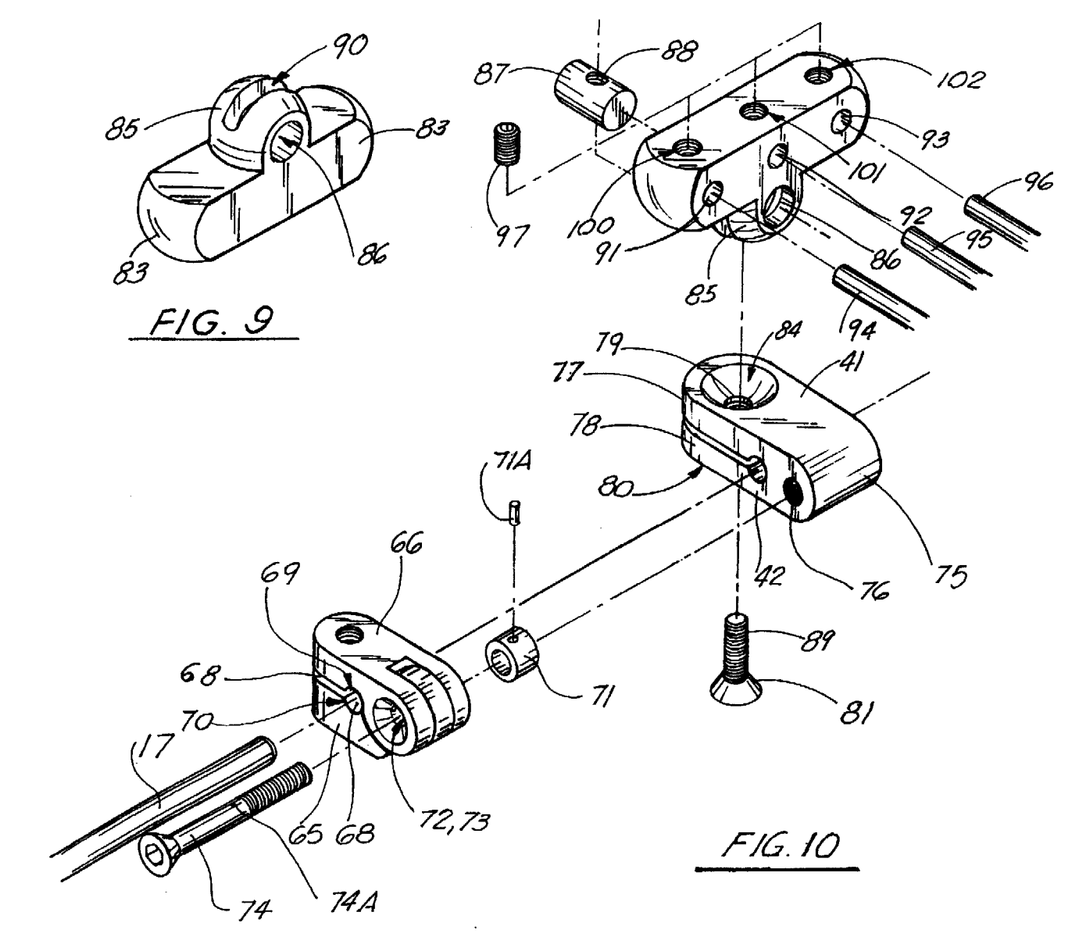
FIG. 9 is a partial perspective view of the second embodiment of the apparatus of the present invention.
FIG. 10 is a partial perspective view of the second embodiment of the apparatus of the present invention illustrating the pin block.

In FIGS. 8–10, the distal radius fixator 10A provides a distraction mechanism that works in combination with a flexion/extension clamp. Distraction clamp mechanism 64 clamps to proximal rod section 17. Distraction clamp 64 includes a pair of clamp members 65, 66 that are hingedly connected together at hinge 67. A cylindrically shaped recess 68 is defined upon a closure of distraction clamp 64 as shown in FIG. 7. Each clamp member 65, 66 provides a respective half cylinder shaped slot 69, 70 that together define the cylindrical recess 68 upon closure as shown in FIG. 7.

Hinge 67 includes aligned openings in each clamp member 65, 66 that align and mount to bushing 71. Each of the clamp members 65, 66 has an opening 72, 73 respectively that fits over bushing 71. Each clamp member 65, 66 opening 72, 73 is cylindrically shaped and sized to closely fit the external diameter of bushing 71.

Figure 5:
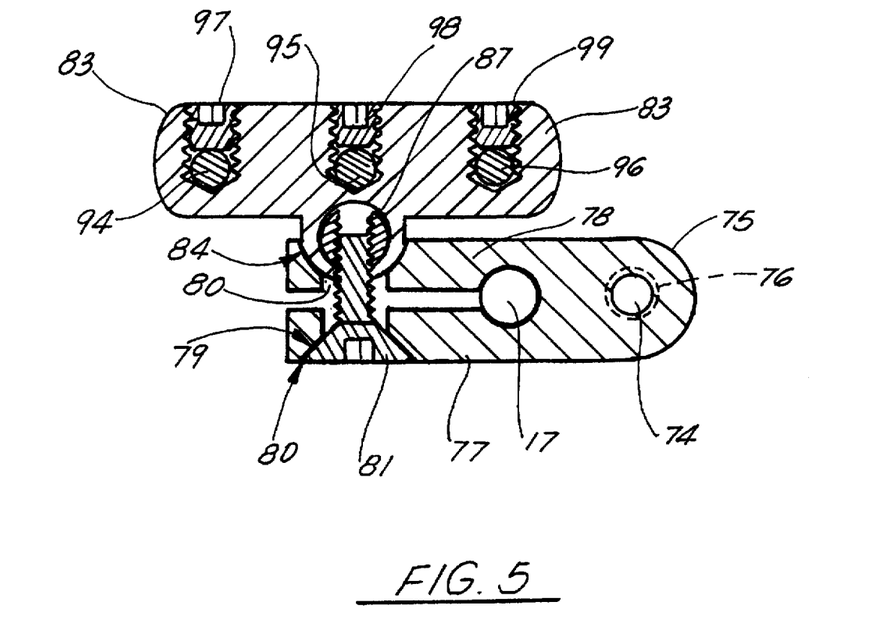
FIG. 5 is a partial sectional view of a second embodiment of the apparatus of the present invention.
Figure 6:
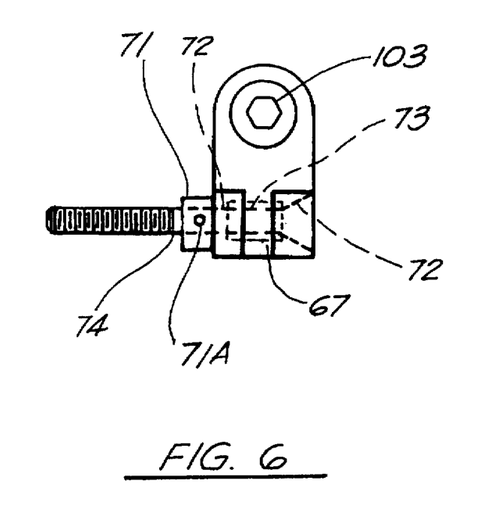
FIG. 6 is a partial sectional view of the second embodiment of the apparatus of the present invention.

Countersunk distraction clamp bolt 74 extends through bushing 71 and engages metacarpal clamp 75 at internally threaded cylindrical opening 76. Clamp 75 includes a pair of spaced apart flanges 77, 78. Each flange 77, 78 provides an opening 79, 80 respectively for accommodating bolt 81. The clamp 75 includes a generally cylindrically shaped slot 82 that is generally parallel to threaded opening 76 and bolt 74 as shown in FIG. 5. Slot 82 engages distal section 17 of rod 15 during use.

Metacarpal pin block 83 attaches to metacarpal clamp 75 at hemispherical recess 84. Metacarpal pin block 83 provides a correspondingly shaped hemispherical projection 85 that engages recess 84 as shown in FIGS. 5 and 9. A cylindrically shaped opening 86 receives pin 87. Pin 87 has internally threaded opening 88 for receiving the threaded shaft 89 of machine screw 81 as shown in FIGS. 5 and 9.

Hemispherical projection 85 has an arcuate slot 90 that allows threaded shaft 89 of screw 81 to pass therethrough as shown in FIG. 5. This allows the projection 85 to articulate with respect to recess 84 and metacarpal clamp 75. Metacarpal pin block 83 includes a plurality of openings 91, 92, 93 that accommodate a plurality of bone pins such as the pins 94, 95, 96 as shown in FIGS. 5 and 8. Pins 94, 95, 96 are surgically affixed to the patient's bone tissue as seen in FIG. 8. Set screws 97, 98, 99 are used to affix each pin 94, 95, 96 to pin block 83. Each set screw 97, 98, 99 travels in a threaded opening 100, 101, 102 respectively of pin block 83.

In order to articulate pin block 83 relative to clamp 75, the user simply loosens machine screw 81. This allows articulation of block 83 in multiple directions and into multiple angular positions with reference to claim 75. Pin block 83 is free to rotate and pivot with reference to clamp 75 when machine screw 81 is loosened. Clamp 75 can be attached to rod 17 as shown in FIG. 5. Clamp 75 can also travel longitudinally along rod 17 for adjustment. Distraction can be achieved by fixedly clamping distraction clamp 65 to rod end 17 by tightening screw 103. A loosening of screw 103 allows clamp 65 to be adjusted into desired positions on rod end 17. Once screw 103 is tightened, the user can move clamp 75, the attached pins 94, 95, 96 and the surgically pinned metacarpals 14 relative to clamp 64 by rotating screw 74 thereby accomplishing the desired distraction.

Figure 11:
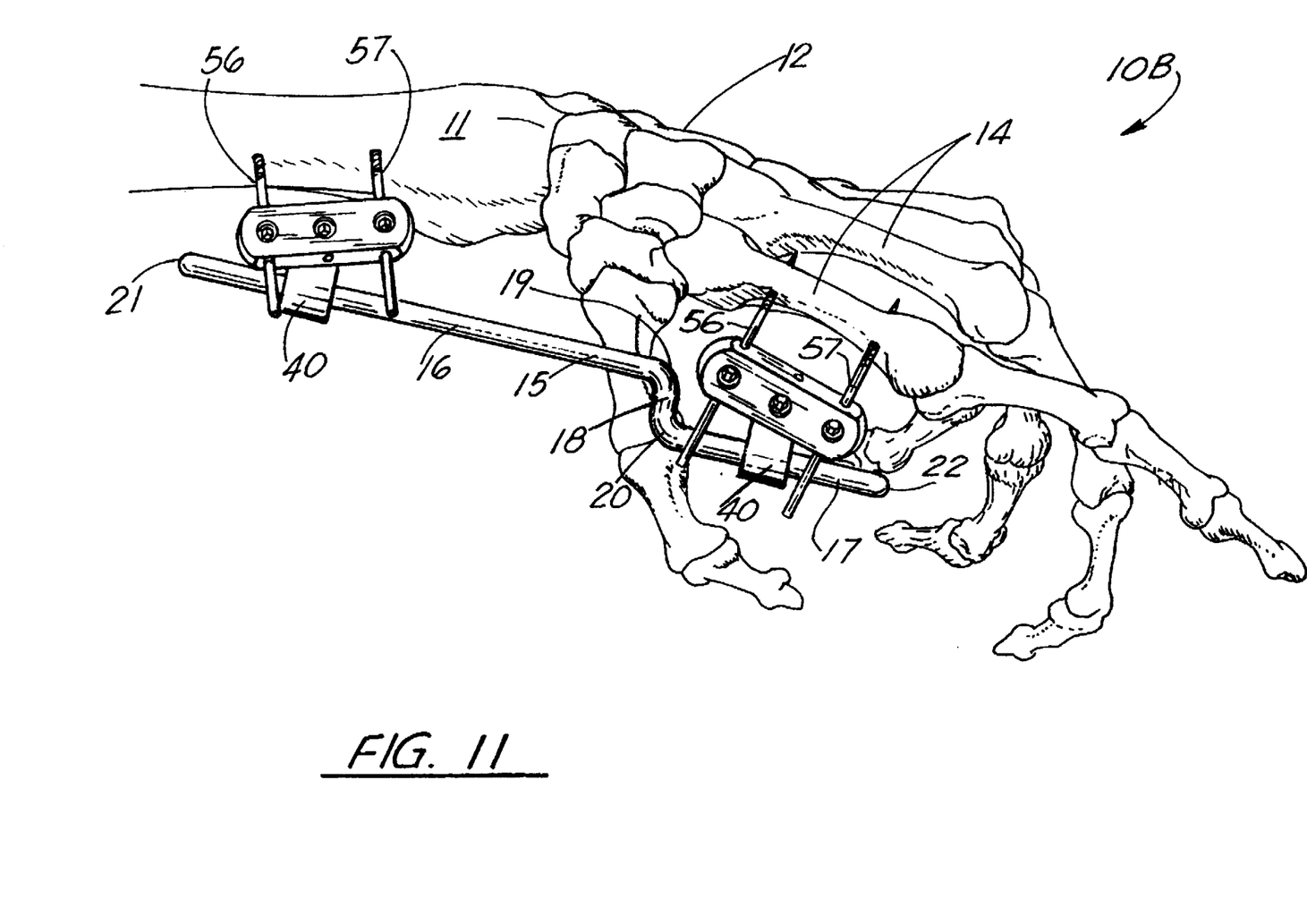
FIG. 11 is a perspective view of a third embodiment of the apparatus of the present invention.

FIG. 11 shows a third embodiment of the apparatus of the present invention, designated generally by the numeral 10B. Fixator apparatus 10B utilizes rod 15 having proximal 16 and distal sections 16, 17 and the verse section 18 as with the embodiments 10, 10A. FIG. 11 uses two clamps such as clamp assembly 40 of FIG. 3. In FIG. 11, the fixator apparatus could alternatively use two articulating clamps that each include clamps 75, the pin block 83, and bone pins 94, 95, 96. Thus, the clamps 75, pin blocks 83 and pins 94, 95, 96 but without the distraction parts of FIGS. 6-7. The rod and support means as above described are configured so that the volar tilt is achieved by rotating the distal rod section relative to the proximal rod section and the support means are rotatable with respect to the rod.

The following table lists the parts numbers and parts descriptions as used herein and in the drawings attached hereto.

PARTS LIST

| Part Number | Description |
| --- | --- |
| 10 | distal radius fixator |
| 10A | distal radius fixator |
| 10B | distal radius fixator |
| 11 | distal radius |
| 12 | wrist |
| 13 | hand |
| 14 | metacarpals |
| 15 | rod |
| 16 | proximal rod section |
| 17 | distal rod section |
| 18 | transverse rod section |
| 19 | bend |
| 20 | bend |
| 21 | rod end |
| 22 | rod end |
| 23 | U-shaped portion |
| 24 | cap screw |
| 25 | radius pin clamp |
| 26 | radius pin |
| 27 | radius pin |
| 28 | clamp section |
| 29 | clamp section |
| 30 | pivot |
| 31 | opening |
| 32 | slot |
| 33 | sleeve |
| 34 | opening |
| 35 | set screw |
| 36 | threaded bore |

PARTS LIST -continued

| Part Number | Description |
| --- | --- |
| 37 | head |
| 38 | shank |
| 39 | external thread |
| 40 | metacarpal pin clamp |
| 41 | clamp section |
| 42 | clamp section |
| 43 | U-shaped portion |
| 44 | cap screws |
| 45 | shank |
| 46 | frustroconical section |
| 47 | slot |
| 48 | opening |
| 49 | pin holder |
| 50 | upper surface |
| 51 | lower surface |
| 52 | threaded opening |
| 53 | threaded opening |
| 54 | set screw |
| 55 | set screw |
| 56 | pin |
| 57 | pin |
| 58 | opening |
| 59 | opening |
| 60 | threaded opening |
| 61 | annular collar |
| 62 | beveled annular surface |
| 63 | opening |
| 64 | distraction clamp mechanism |
| 65 | clamp member |
| 66 | clamp member |
| 67 | hinge |
| 68 | cylindrical recess |
| 69 | slot |
| 70 | slot |
| 71 | bushing |
| 72 | opening |
| 73 | opening |
| 74 | distraction clamp bolt |
| 75 | metacarpal clamp |
| 76 | internally threaded opening |
| 77 | flange |
| 78 | flange |
| 79 | opening |
| 80 | opening |
| 81 | machine screw |
| 82 | slot |
| 83 | metacarpal pin block |
| 84 | hemispherical recess |
| 85 | hemispherical projection |
| 86 | cylindrical opening |
| 87 | cylindrical bushing |
| 88 | internally threaded opening |
| 89 | threaded shaft |
| 90 | arcuate slot |
| 91 | opening |
| 92 | opening |
| 93 | opening |
| 94 | pin |
| 95 | pin |
| 96 | pin |
| 97 | set screw |
| 98 | set screw |
| 99 | set screw |
| 100 | internally threaded opening |
| 101 | internally threaded opening |
| 102 | internally threaded opening |
| 103 | set screw |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An external fixator apparatus for distal radius fractures, comprising:
   a) a unitary one-piece elongated support rod having a distal end and a proximal end of a generally uniform, transverse cross section that includes a central rod section and proximal and distal longitudinally extending rod end sections and an outer surface, the proximal and distal rod sections being offset from each other and the central rod section connecting the distal end of the proximal rod end section to the proximal end of the distal rod end section;
   b) radius fixation pins for engaging the patient's radius bone tissue;
   c) at least one radius support member rotatably supported upon the proximal rod section for externally supporting the patient's distal radius, said support member including means for holding the radius fixation pins, said support member having a uniformly shaped radius support member bore that conforms to the outer surface of the rod enabling longitudinal travel of the radius support member along the length of the proximal rod section and allowing simultaneous rotation of the support member upon the rod at the radius support member bore and relative to the radius fixation pins;
   d) metacarpal fixation pins for engaging the patient's metacarpal bone tissue; and
   e) a hand support member rotatably supported upon the distal rod section for externally supporting the patient's hand, said hand support member including means for holding the metacarpal fixation pins, said hand support member having a hand support member bore that conforms to the outer surface of the rod enabling longitudinal travel of the hand support member along the length of the distal rod section and allowing rotation relative to the rod at the hand support member bore and relative to the metacarpal fixation pins.

2. The fixator apparatus of claim 1 wherein the proximal and distal rod sections are generally parallel.

3. The fixator apparatus of claim 1 wherein the radius support member includes a clamping portion for clamping the proximal rod section.

4. The fixator apparatus of claim 1 wherein the hand support member includes a clamping portion for clamping the distal rod section.

5. The fixator apparatus of claim 1 wherein there are a pair of radius support members that are rotatably connected to one another.

6. The apparatus of claim 1 wherein there are a pair of hand support members that are rotatably connected to one another.

7. The apparatus of claim 1 wherein the hand support member includes means for translating a portion of the radius relative to the rod.

8. The apparatus of claim 1 wherein the proximal rod section has a central longitudinal axis and the radius support member and rod are so configured that the distal rod section is rotatably connected during use to the radius support member.

9. The apparatus of claim 1 wherein the hand support member is slidable upon the distal rod section during use for distracting the ligaments of the patient's wrist.

10. The apparatus of claim 1 wherein the rod and support members are so configured that volar tilt is achieved by rotating the distal rod section relative to the proximal rod section when the support members are rotated upon the rod.

11. An external fixator apparatus for distal radius fractures, comprising:
    a) a unitary one-piece elongated support rod having a distal end and a proximal end of a generally uniform transverse cross section that includes a central rod section and proximal and distal longitudinally extending rod end sections and an outer surface, the proximal and distal rod end sections being offset from each other and the central rod section connecting the distal end of the proximal rod end section to the proximal end of the distal rod end section;
    b) radius fixation pins for engaging and supporting the patient's radius bone tissue at selected positions;
    c) a radius support clamp that is movably supported upon the proximal rod section for externally supporting the patient's distal radius, said radius support clamp including means for holding the radius fixation pins, said radius support clamp having a hollow open ended radius support clamp bore that surrounds the support rod and that is configured to enable longitudinal travel of the radius support clamp the length of the proximal rod section and to allow simultaneous rotation of the clamp relative to the rod at the radius support clamp bore and relative to the radius fixation pins;
    d) metacarpal fixation pins for engaging the patient's metacarpal bone tissue;
    e) a hand support clamp movably supported upon the distal rod section for externally supporting the patient's hand, said hand support clamp including means for holding the metacarpal fixation pins and a hollow bore hand support clamp that surrounds the support rod, said hand support clamp enabling longitudinal travel of the radius support clamp along the length of the proximal rod section and allowing simultaneous rotation relative to the rod and relative to the metacarpal fixation pins; and
    f) each of the clamps being slidably and rotatably mounted on the rod so that each clamp can adjustably move between an end of the rod and the center portion of the rod, each of the clamps having first and second portions that rotate upon one another.

12. The external fixator of claim 11 wherein each of the clamps has a rod opening sized and shaped to conform to the rod.

13. The external fixator of claim 11 wherein the proximal and distal rod sections are generally parallel.

14. The external fixator of claim 11 wherein the hand support clamp rotatably attaches to the distal rod section.

15. The external fixator of claim 11 wherein at least one of the clamps can slide upon the rod.

* * * * *